(12) United States Patent
Sparacino et al.

(10) Patent No.: US 10,357,207 B2
(45) Date of Patent: Jul. 23, 2019

(54) ALERT SYSTEM FOR HYPO AND HYPERGLYCEMIA PREVENTION BASED ON CLINICAL RISK

(71) Applicant: DexCom, Inc., San Diego, CA (US)

(72) Inventors: Giovanni Sparacino, Padua (IT); Claudio Cobelli, Padua (IT); Stefania Guerra, Carre (IT); Andrea Facchinetti, Padua (IT); Michele Schiavon, Chioggia (IT)

(73) Assignee: DexCom, Inc., San Diego, CA (US)

( * ) Notice: Subject to any disclaimer, the term of this patent is extended or adjusted under 35 U.S.C. 154(b) by 41 days.

(21) Appl. No.: 15/239,712

(22) Filed: Aug. 17, 2016

(65) Prior Publication Data
US 2016/0361028 A1 Dec. 15, 2016

Related U.S. Application Data

(63) Continuation of application No. 13/661,393, filed on Oct. 26, 2012, now Pat. No. 9,439,602.

(60) Provisional application No. 61/551,773, filed on Oct. 26, 2011.

(51) Int. Cl.
  *A61B 5/00* (2006.01)
  *A61B 5/145* (2006.01)
  *G16H 50/30* (2018.01)

(52) U.S. Cl.
  CPC ........ *A61B 5/7275* (2013.01); *A61B 5/14532* (2013.01); *A61B 5/743* (2013.01); *A61B 5/746* (2013.01); *A61B 5/7405* (2013.01); *A61B 5/7455* (2013.01); *G16H 50/30* (2018.01)

(58) Field of Classification Search
  None
  See application file for complete search history.

(56) References Cited

U.S. PATENT DOCUMENTS

| 6,175,752 | B1 | 1/2001 | Say et al. |
| 2010/0179409 | A1 | 7/2010 | Kamath et al. |
| 2011/0077494 | A1 | 3/2011 | Doniger et al. |
| 2011/0193704 | A1 | 8/2011 | Harper |
| 2011/0201911 | A1 | 8/2011 | Johnson et al. |

OTHER PUBLICATIONS

Facchinetti, et al., "Reconstruction of Glucose in Plasma from Interstitial Fluid Continuous Glucose Monitoring Data: Role of Sensor Calibration," Journal of Diabetes Science and Technology vol. 1, Issue 5, Sep. 2007, pp. 617-623.*

(Continued)

*Primary Examiner* — Eric J Messersmith
(74) *Attorney, Agent, or Firm* — Knobbe Martens Olson & Bear, LLP

(57) ABSTRACT

A device for generating alerts for Hypo and Hyperglycemia Prevention from Continuous Glucose Monitoring (CGM) determines a dynamic risk based on both information of glucose level and a trend obtainable from a CGM signals. The device includes a display whose color depends on the DR (for example, red for high DR, green for low risk). When DR exceeds a certain threshold, alerts are generated to suggest the patient to pay attention to the current glucose reading and to its trend, both of which are shown on the display in numbers and symbols (e.g. an arrow with different slope or color).

11 Claims, 3 Drawing Sheets

(56) References Cited

OTHER PUBLICATIONS

Sparacino, et al. "WINSTODEC: a stochastic deconvolution interactive program for physiological and pharmacokinetic systems," Computer Methods and Programs in Biomedicine 67 (2001) 67-77 (Year: 2001).*

Vicini, et al., "Estimation of endogenous glucose production after a glucose perturbation by nonparametric stochastic deconvolution," Computer Methods and Programs in Biomedicine 52 (1997) 147-156 (Year: 1997).*

* cited by examiner

US 10,357,207 B2

ALERT SYSTEM FOR HYPO AND HYPERGLYCEMIA PREVENTION BASED ON CLINICAL RISK

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. patent application Ser. No. 13/661,393, filed on Oct. 26, 2012, which claims the benefit of U.S. Provisional Application No. 61/551,773, filed on Oct. 26, 2011. Each of the aforementioned applications is incorporated by reference herein in its entirety, and each is hereby expressly made a part of this specification.

FIELD OF THE INVENTION

The present invention relates to glucose monitoring systems and, more specifically, to a method to generate alerts, based on a measure of the clinical risk associated to both glucose level and current trend, for hypoglycemia and hyperglycemia prevention in patients wearing such devices.

DESCRIPTION OF THE RELATED ART

Diabetes is a chronic disease characterized by impaired/absent production of a hormone, insulin, which lowers the glucose concentration in blood after a meal. The standard therapy for diabetes is based on insulin and drugs administration, diet and physical exercise, tuned according to self-monitoring of blood glucose (SMBG) levels 3-4 times a day. Given the inefficiency of SMBG approach in capturing the actual extent of glucose dynamics during the daily life, glycaemia (glucose concentration in blood, BG) often exceeds the normality range (70-180 mg/dl). Episodes of hypoglycemia (BG<70 mg/dl) and hyperglycemia (BG>180 mg/dl) are dangerous for the patient mainly in the short term and in the long term for respectively. Short-term consequences are dramatic since they may lead to diabetic coma, while prolonged periods of hyperglycemia are associated to the development of complications such as the diabetic retinopathy and nephropathy.

In the last decade, new devices have become available for the continuous monitoring of the glycaemia. Minimally invasive Continuous Glucose Monitoring (CGM) devices, such as the Dexcom Seven plus, the MiniMed Paradigm Real-Time and Non Invasive Continuous Glucose Monitoring (NI-CGM) are becoming available for clinical practice, providing a measurement of glucose concentration every 1-5 minutes. Such devices are crucial, since they provide a real-time and almost continuous information on patient's glycemic concentration. In addition, most of these devices are provided with an alert generator system, which generates a visual/acoustic alert when hypoglycemic and hyperglycemic thresholds are crossed by the current glycaemia, allowing prompt detection of such threatening events. More important, the almost continuous feature of CGM output allows the use of prediction techniques to anticipate the crossing, and eventually alert the patient of the upcoming event.

Therapeutic actions, such as injection of insulin correction boluses to revert a condition of hyperglycemia- or carbohydrates intake to treat hypoglycemia, cannot avoid exposure of the patients to events that can be threatening, either in the long or short term. In fact, insulin requires about an hour to be effective and to induce appreciable decrease in glucose concentration. Also, carbohydrates take time to reach the blood stream in order to compensate the effects of hypoglycemia. In this framework, generating an alert ahead of the time could give the patient enough time for the therapeutic actions to be effective in avoiding the threats of the event itself.

It is important to provide the patient with information about his/her glycemic status in a smart manner, e.g. by supplying information on the current "clinical risk". Conceptually, the clinical risk is a measure of the severity of a specific glycemic condition, which depends mainly on the glucose level, but might be influenced also by other factors, such as glucose trend and possibly the quantity of insulin present in the patient's body. In particular, when evaluating the "clinical risk" to which the patient is exposed, one should consider not only the glycemic level but also its trend. Notably, a device which raises alarms on the basis of glucose sensor information and critical risk, should exploit technologies embeddable on a small PDA platform.

CGM Devices and their Alert Systems

Minimally invasive Continuous Glucose Monitoring (CGM) devices currently available in the market, such as the Dexcom Seven Plus (Dexcom Inc., San Diego, Calif.), the MiniMed Paradigm Real-Time (Medtronic Inc., Northridge, Calif.), the Guardian Real-Time (Medtronic Inc., Northridge, Calif.), and the FreeStyle Navigator (Abbott Diabetes Care, Alameda, Calif.), are provided with a visual/acoustic alert generator system that warns the patient when hypoglycemic or hyperglycemic thresholds are crossed. This type of alert is based on the current glycemic value measure by the sensor only. The FreeStyle Navigator or the MiniMed Paradigm Real-Time also embeds another alert generator system for hypoglycemia and hyperglycemia, based on the projection of current glucose level and trend. In particular, the projection method employed in the MiniMed Paradigm Real-Time estimates the current trend using a Savitzky-Golay finite impulse response derivative filter, which is multiplied by a prediction horizon of 5-30 minutes.

Research on Glucose Prediction Algorithms: State of the Art

The real-time prevention of hypo/hyperglycemic events is a natural online application of CGM. As a matter of fact, a few years after the appearance of CGM sensors in the market, some projection methods were proposed to generate alerts when the actual trend of the glucose concentration profile suggested that hypoglycemia was likely to occur within a short time. In Choleau et al., for instance, an hypoalert is generated when the future glycemic concentration, obtained on the basis of first-order linear extrapolation of the last two/three glucose samples, is forecasted to cross the hypoglycemic threshold within 20 min. Similar methods are implemented in commercial devices, with the aim of delivering alerts for dangerous trends.

Also generation of hypo/hyperalerts can be obtained by means of ahead-of-time prediction of glucose concentration calculated from past CGM data. Sparacino et al., demonstrated that simple prediction algorithms based on model with a reduced number of parameters, i.e. either first-order polynomial or first-order auto-regressive (AR(1)) models, with time-varying parameters identified by least squares (LS) using a fixed forgetting factor, are suitable for predicting glycaemia ahead in time with a sufficient accuracy, with a PH of 30 and 45 min. Eren-Oruklu et al. developed prediction algorithms based on AR(3) and ARMA(3,1) models, with time-varying parameters identified by LS, using a forgetting factor μ which could be modulated according to the glucose trend. Reifman et al. proposed a predictor based on an AR(10) model, with time-invariant and subject-invariant parameters identified by regularized LS. Similarly, Gani et al. developed a prediction strategy based on an AR(30) model with time-invariant parameters identified by regularized LS on pre-filtered data. Finan et al. proposed a predictor based on an ARX(3) model with exogenous inputs given by ingested carbohydrates and insulin medications, both with time-invariant and time-variant parameters. Palerm and Bequette, after having posed the problem in a state-space setting, used the Kalman filtering methodology to predict glucose level after a given PH, using a double integrated random walk as prior for glucose dynamics.

Recently, NN models have been the subject of some investigations for glucose prediction. Perez-Gandia et al. developed a feed-forward NN for glucose prediction, trained and tested with 3 different PHs, i.e. 15, 30, and 45 min. More recently, Pappada et al. proposed a NN approach to predict glycaemia with a PH of 75 min. Finally, a preliminary study carried out on a limited dataset consisting of only one patient was developed by Eskaf et al. Inputs of their NN model include the first-order differences of the glycemic time series, and information on meals, insulin and physical exercise, extracted directly from the blood glucose time-series, by modeling the glycemic level as a dynamic system.

Margin of Improvements of CGM Devices

Even if several predictive models have been developed to forecast in real time the future glucose level measured by a CGM device, none of the CGM devices currently available in the market is provided with an alert generation system which generates preventive hypoglycemic and hyperglycemic alerts based on the concept of current clinical risk associated to the glycemic value and its trend.

Clinical Risk Measured by the Dynamic Risk Concept

It has been suggested by Kovatchev and colleagues that the study of glucose concentration time series should take into account that the glycemic range is asymmetric, with the "hypo range" much narrower than the "hyper range" with a much faster increase of health threats when moving deeper in the first vs. the latter range. Also, the distribution of glucose concentration values is skewed within the range. In the literature, transformations of the glucose scale into penalty scores have been proposed by Kovatchev, by Hill et al (Glycemic Risk Assessment Diabetes Equation, GRADE), and by Rodbard (Index of Glycemic Control, ICG). These scores are able to equally weight hypo and hyperglycemic episodes. As an example of risk score, we consider Kovatchev's formulation. In this approach, a nonlinear transformation converts every single glucose reading into a "static" risk value, which puts more emphasis on values within the clinically critical regions of hypo and hyperglycemia than in the safe region of normo-glycaemia.

The above mentioned transformations of glucose levels and the correspondent indexes are "static", i.e. a given glycemic level is associated to a specific penalty or risk score.

Recently a modification of the mathematical definition of risk associated with glucose levels has been proposed by Guerra et al. in order to include in the concept of risk not only the actual glycemic level, but also the glucose trend. Consider for example a glycemic level of 65 mg/dl (mild hypoglycemia) with decreasing or increasing trend. The first case (decreasing trend, negative time derivative) refers to a more threatening condition, since the patient is heading deeper into the hypoglycemic region while in the second case (increasing trend, positive time derivative) the patient is recovering towards the normo-glycaemia. The new risk function, called the Dynamic Risk (DR) includes this information, assigning higher risk to situation in which the trend is leading to a dangerous zone. In particular the risk is increased when glucose concentration is close to or in the hypoglycemic range with decreasing trend and is close to or in the hyperglycemic range with increasing trend. It has been proved that the DR as formulated is intrinsically predictive, since it allows for alert generation about 10 minutes before the actual threshold crossing. Several mathematical formulations/structures of DR can be implemented exploiting variants of those proposed.

SUMMARY OF THE INVENTION

The disadvantages of the prior art are overcome by the present invention which, in one aspect, is a system able to measure the glycaemia in an almost continuous manner (one measurement every 1-10 minutes), which employs an algorithm to generate preventive hypoglycemic and hyperglycemic alerts based on the Dynamic Risk concept associated to both current glucose level and trend. The system alerts the patient with a sensorial alarm that can be tactile, visual or auditory. In a preferred embodiment the system will have a color monitor with a colored blinking/pulsing back-light option which will be activated when an alarm is raised.

In one aspect, the invention is a system for alerting a patient of hypoglycemia and hyperglycemia risk that includes a continuous glucose monitoring (CGM) device configured to determine periodically a glucose level in the patient, thereby generating a series of glucose levels. A dynamic risk estimation module is configured to: evaluate a differential change in glucose level over time (dg/dt) based on the series of glucose levels; generate a smoothed glucose level that is indicative of the series of glucose levels; calculate dg/dt based on the series of smoothed glucose levels; and estimate a dynamic risk based on the smoothed CGM and estimated dg/dt. A comparison circuit compares the dynamic risk to a predetermined threshold. A device monitor that is configured to generate a display representative of the smoothed CGM and that is also configured to generate a perceptible alarm when the dynamic risk is greater than the predetermined threshold.

Additionally, a circuit calculates an angle $\alpha$ that is a function of dg/dt and the device monitor is also displays an arrow that is angled from horizontal by the angle $\alpha$. The perceptible alarm could be, for example, a blinking display, a brightly colored display, a vibratory alarm, an audible alarm, or any combination of these alarms. The display may also show different smoothed CGM values as corresponding different colors. The display may also display a trend box that indicates a CGM data trend.

In another aspect, the invention is a method of monitoring glucose in a patient, in which a periodic series of glucose levels in the patient is received from a continuous glucose monitoring (CGM) device. A differential change in glucose level is evaluated over time (dg/dt) based on the series of glucose levels. A smoothed glucose level that is indicative of the series of glucose levels is generated. The series of glucose levels is used to calculate dg/dt. A dynamic risk based on the smoothed CGM and dg/dt is estimated. The dynamic risk is compared to a predetermined threshold. A display representative of the smoothed CGM is generated. A perceptible alarm is generated when the dynamic risk is greater than the predetermined threshold.

These and other aspects of the invention will become apparent from the following description of the preferred embodiments taken in conjunction with the following drawings. As would be obvious to one skilled in the art, many variations and modifications of the invention (including variations of mathematical structures and parameters in DR definition) may be effected without departing from the spirit and scope of the novel concepts of the disclosure.

DETAILED DESCRIPTION OF THE INVENTION

Figure 1:
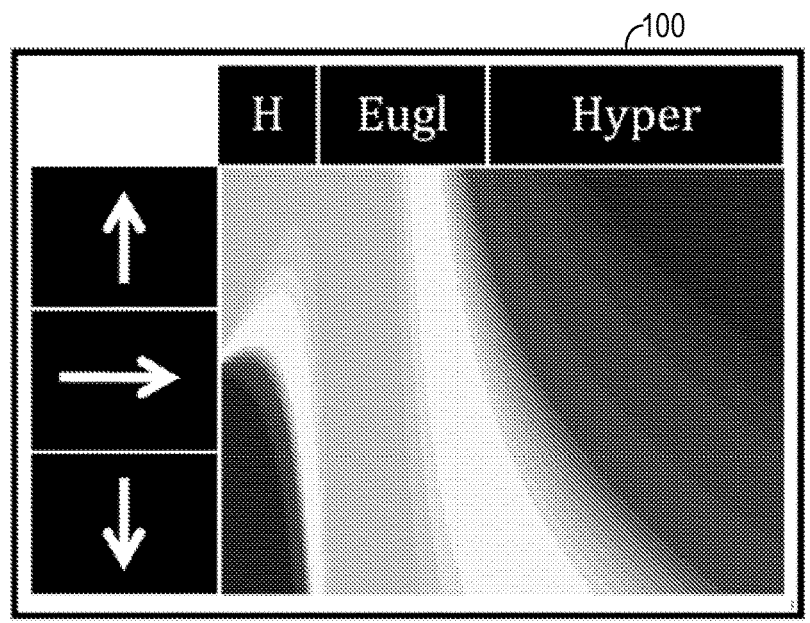
FIG. 1 is a diagram showing a dynamic risk space: example of colors that can be associated to different glucose levels (x axis) and first time derivative value (y axis).

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

A device for the continuous monitoring of glycaemia, either minimally or noninvasive, will be employed. An algorithm for the evaluation of the clinical risk measure called Dynamic Risk (DR) will be embedded in the device and will drive the activation of the alerts.

The embodiment of the invention here proposed includes in a DR evaluation method, which comprises both a static component able to equally weight hypo and hyperglycemic events, and a component which is able to account for the trend of the signal. The algorithm predicts threshold crossings, i.e. it detects and predicts approaches to risky zones of hypo/hyperglycemia with a significant temporal gain (e.g., of 10 or more minutes). One embodiment of the device includes a monitor where the glycemic level is shown along with a trend arrow, which can change its slope and color according to the estimated clinical risk. In one preferred setting the display background can be highlighted with different colors and can blink when threatening conditions are approaching.

Estimation of the Dynamic Risk in Real Time

The algorithm for the assessment of the clinical risk by the computation of the Dynamic Risk receives as an input:
The glycemic level measured by the CGM device
The estimate of the first time derivative
Parameters defining the relative importance of risk associated to glucose level and glucose trend.

The dynamic risk (DR) should preferably respect following equations:

$$\begin{cases} |DR| > r(g) & \text{if } \frac{dg}{dt} \cdot SR(g) > 0 \\ |DR| < r(g) & \text{if } \frac{dg}{dt} \cdot SR(g) < 0 \end{cases}$$

Where r(g) is a score function that maps glucose levels in risk scores and dg/dt is the differential change in glucose level over the differential change in time, estimated possibly by means of a regularized deconvolution algorithm. As example Kovatchev's risk function can be used: $r(g)=10f(g)^2$ with $f(g)=\gamma \cdot [(\ln(g))^\alpha - \beta]$; α, β, γ being scalars equal to 1.084, 5.381 and 1.509 (assuming glucose expressed in mg/dl). The above function r(g) maps the glycemic range [20-600] mg/dl to the (static) risk space range [0–100] [0÷100]. This means that given a specific risk score for glycemic levels per se, a dynamic risk evaluating also the risk associated to the trend will assign higher risk if the trend is leading to threatening zones. In particular, hypoglycemia with decreasing trend and hyperglycemia with increasing trend will be assigned with highest risk. If other DR functions are employed with these characteristics, they should preferably be continuous in the working range.

In one representative embodiment, the Dynamic Risk can be defined as in:

$$DR\left(g, \frac{dg}{dt}\right) = \begin{cases} SR(g) \cdot e^{+\mu \frac{dr}{dt}} & \text{if } SR(g) > 0 \\ SR(g) \cdot e^{-\mu \frac{dr}{dt}} & \text{if } SR(g) < 0 \end{cases}$$

where $$SR(g) = r_h(g) - r_l(g)$$

$$r_l(g) = \begin{cases} r(g) & \text{if } f(g) < 0 \\ 0 & \text{otherwise} \end{cases}$$

$$r_h(g) = \begin{cases} r(g) & \text{if } f(g) > 0 \\ 0 & \text{otherwise} \end{cases}$$

Other structures of DR may be employed, for instance other implementations can be used which is based on the hyperbolic or arctangent:

$$DR_{tanh}\left(g, \frac{dg}{dt}\right) = \begin{cases} SR(g) \cdot \left[\delta \cdot \tanh\left(\alpha \frac{dr}{dt} + \gamma\right) + \beta\right] & \text{if } SR(g) > 0 \\ SR(g) \cdot \left[\delta \cdot \tanh\left(-\alpha \frac{dr}{dt} + \gamma\right) + \beta\right] & \text{if } SR(g) < 0 \end{cases}$$

$$DR_{atan}\left(g, \frac{dg}{dt}\right) = \begin{cases} SR(g) \cdot \left[\delta \cdot \text{atan}\left(\alpha \frac{dr}{dt} + \gamma\right) + \beta\right] & \text{if } SR(g) > 0 \\ SR(g) \cdot \left[\delta \cdot \text{atan}\left(-\alpha \frac{dr}{dt} + \gamma\right) + \beta\right] & \text{if } SR(g) < 0 \end{cases}$$

An important issue to be address is how the first time derivative is computed in the device, since measurement noise can heavily affect the quality of the estimation of the first derivative signal. If the signal to noise ratio (SNR) is sufficiently high, i.e. the noise has low amplitude with respect to the glucose signal, one can evaluate the derivative as first order finite differences. If the SNR is low and the noise component is significant, a deconvolution based approach for the simultaneous estimation of the first time derivative and of a smoothed version of the CGM signal is used. The method should be implemented in a preferred embodiment.

As stated above, the DR is intrinsically predictive, since it amplifies the glycaemia in the risk space whenever the glycaemia itself is approaching a clinically critical region. In a preferred embodiment the DR can be exploited for its predictive features as follows:

As standalone predictive tool: evaluate the DR of the glycemic level as it is measured by the (NI)-CGM.

To evaluate the clinical risk of a predictive profile: evaluate the DR of a predicted glycemic profile. For example we propose an embodiment where a short-term prediction of the glycemic profile is obtained via Kalman Filter, and then translated into the DR space. In this way one can sum up the temporal gain obtained via simple prediction with the localized amplification where the predicted glycaemia is heading towards a hypo/hyper region.

To modulate on the basis of the DR of the glucose concentration the visual/acoustic level of the hypoglycemic and hyperglycemic alarms generated by either the CGM measured value or the predicted CGM value.

To determine when the visual/acoustic alert status should be stopped (e.g. when the CGM profile is passing from the hypoglycemic to the euglycemic range with increasing trend, or from the hyperglycemic to the euglycemic range with decreasing trend).

As a signal to be fed to a prediction algorithm: perform a prediction of the DR profile with literature prediction algorithms, e.g. the autoregressive model of order one presented in Sparacino et al. (IEEE Trans Biomed Eng 2007) or the neural network presented in Zecchin et al. (IEEE Trans Biomed Eng 2012). The system should raise an alarm whenever the predicted profile, Clinical DR, or Clinical DR of the predicted glycemic profile exceeds a threshold, which could be fixed in the CGM device, or settable by the patient, or individualized on from user to user. The alarm can be given in form of sound, voice, vibration, constant/blinking/pulsing light placed on the devices or on its monitor, or in any other way that is usually employed by commercial devices.

Output for the Patient and Display

Figure 2:
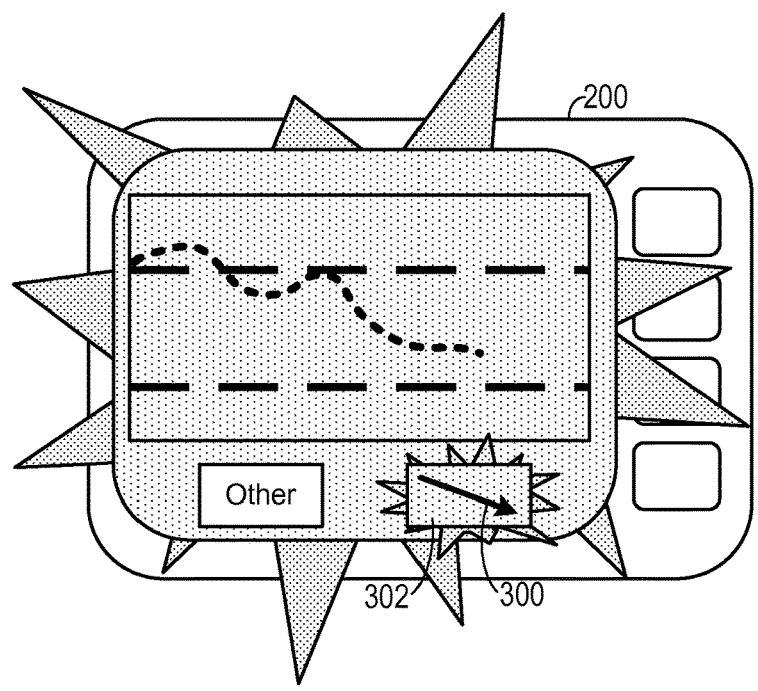
FIG. 2 is a diagram showing a display in an alert mode. In case of alert (threshold crossing of predicted profile or of DR associated to actual glucose trend and level), the display will be colored with the actual DR color code and blink.

In the system proposed in this invention, a colored monitor 100 is used as an alert system as explained below. In fact, specific combination of glucose level and trend can be associated to risk color accordingly with DR. For example, a scale of colors can be used considering the following graph (as shown in FIG. 1) (Please note that the different colors are represented in FIG. 1 as different shades of gray.):

In a device monitor 200, the background of the display can be colored accordingly with DR as shown in FIG. 2. In particular, when a threshold, which can be fixed, settable by the user or individualized on the specific user, is crossed and an alert needs to be raised, the background of the screen can pulse in red, or in any appropriate color, warning the patient that he/she is reaching a risky condition.

Figure 3:
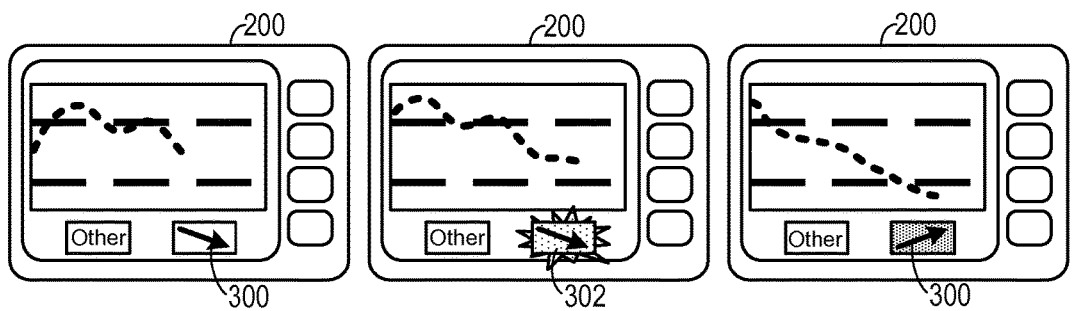
FIG. 3 is a diagram showing several examples of different clinical conditions detected by the continuous glucose monitoring device. [Left] Euglycaemia with almost stable trend: the trend/DR square shows a slightly decreasing arrow on green background. [Center] Hypoglycemia with decreasing trend: the trend/DR square shows a decreasing arrow on red-blinking background. [Right] Hypoglycemia with increasing trend: the trend/DR square shows an increasing arrow on orange background. The color is picked from a color map similar to that on FIG. 1, which assigns a risk color to each pair (glucose-trend).

In another implementation, a colored squared area can be dedicated to the display of an arrow 300 indicating the trend. In a preferred embodiment, the square should blink when the patient is approaching risky regions. An example of such situations is shown in FIG. 3. The color of a trend box 302 could be a function of DR, with higher DR in absolute value are associated to red color, while lower risks are associated to orange yellow and finally green for safe conditions. The arrow 300 displayed in the trend box 302 represents the trend evaluated via a smart algorithm (e.g. via deconvolution via finite differences). The angle from the baseline is a function of the first time derivative of the measured signal.

Figure 4:
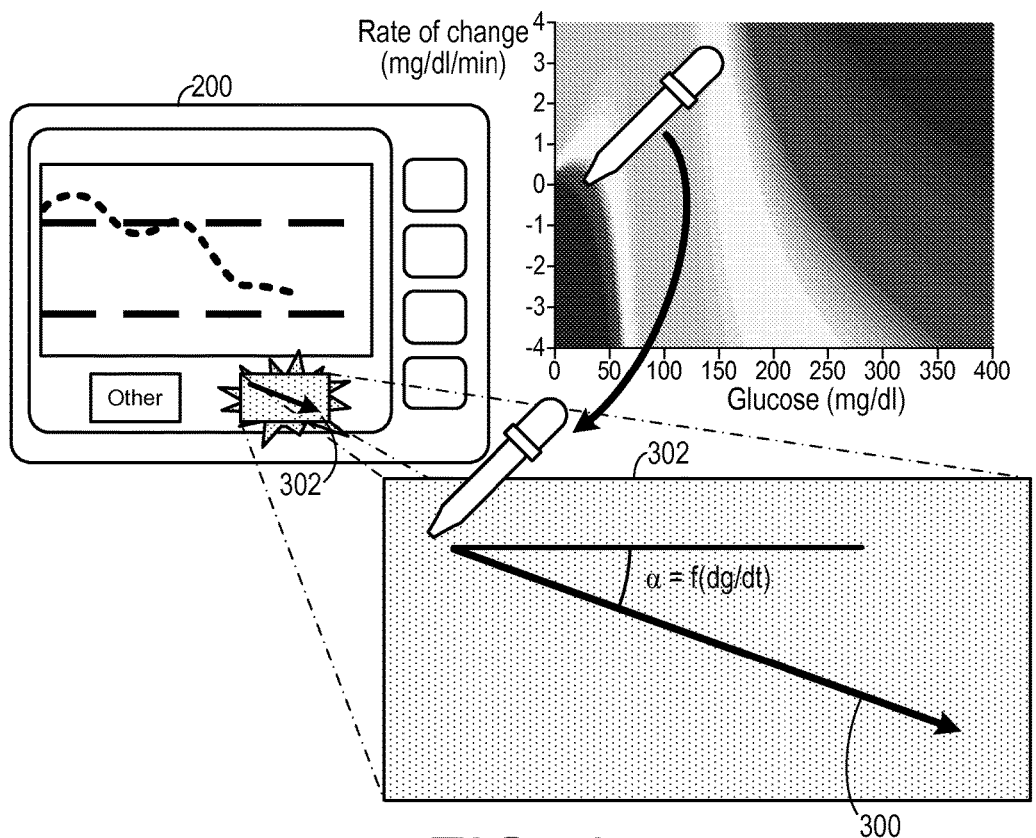
FIG. 4 is a diagram demonstrating a working principle of the trend/DR square. The arrow angle from baseline is a function of the first time derivative. Highest slope (±90° from baseline should be associated to derivatives of ±5 mg/dl or higher; flat arrow should be displayed in stable conditions). The background color of the square should be picked from a color map based on DR: an example is shown in FIG. 1 and reported here for simplicity.

In one embodiment, as shown in FIG. 4, the angle ($\alpha$) of the arrow 300 relative to the horizontal can be proportional to dg/dt. Also, other implementation could comprise a LED light on the device which is activated whenever a risky situation is near.

Figure 5:
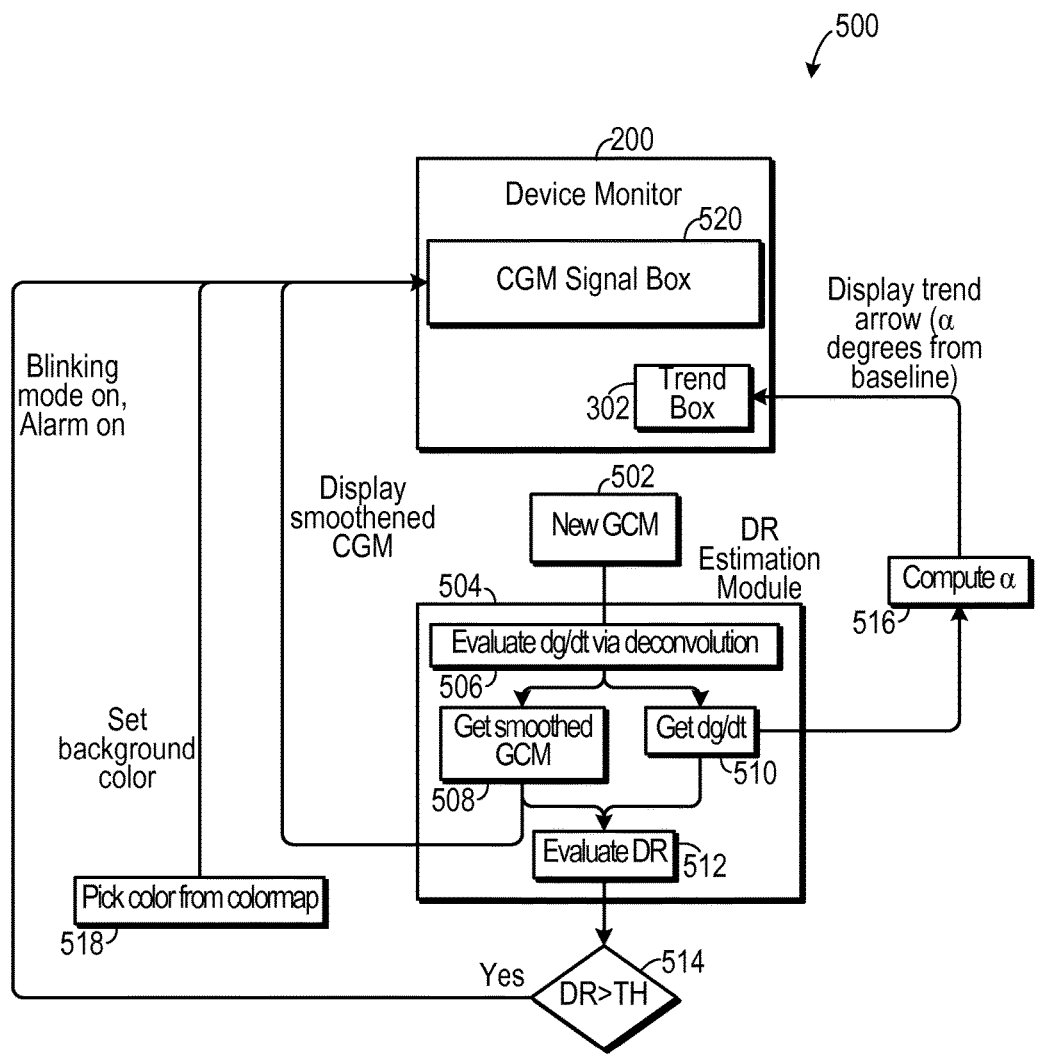
FIG. 5 is a Flow-chart explaining the algorithm driving the display actions.

As shown in FIG. 5, one representative embodiment of an alert system 500 includes a device monitor 200 (as shown in FIGS. 1-4) that includes a CGM signal box display showing data 520 (such as the display shown in FIG. 1) from a continuous glucose monitoring (CGM) device input and a trend box 302. A color map 518 is used to map CGM signals to the CGM signal box 520. The device monitor can include a dynamic risk estimation module 504 (which can be embodied as a digital circuit running a program stored in a digital memory) programmed to receive a new continuous glucose monitoring value 502 from the continuous glucose monitoring device and evaluate the differential change in glucose level over time (dg/dt) 506, generate a smoothed CGM signal 508, which is displayed in the CGM signal box 520. The DR estimation module 504 also calculates the dg/dt to compute 516 the angle $\alpha$ of the arrow in the trend box 302. The DR estimation module 504 then evaluates the dynamic risk (DR) 512 based on the CGM value and dg/dt. If the DR is greater than a threshold 514, then the system generates a blinking display, a brightly colored display, a vibratory alarm, an audible alarm, or a combination of these alarms.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A system for alerting a patient of hypoglycemia and hyperglycemia risk, comprising:
    (a) a continuous glucose monitoring (CGM) device configured to determine periodically a glucose level in the patient, thereby generating a series of glucose levels;
    (b) a dynamic risk estimation module that is configured to:
        (i) evaluate a differential change in glucose level over time (dg/dt) based on the series of glucose levels by employing a deconvolution algorithm;
        (ii) generate a smoothed glucose level that is indicative of the series of glucose levels; and
        (iii) estimate a dynamic risk based on the smoothed CGM and dg/dt;
    (c) a comparison circuit that compares the dynamic risk to a predetermined threshold; and
    (d) a device monitor that is configured to generate a display representative of the smoothed CGM and that is also configured to generate a perceptible alarm when the dynamic risk is greater than the predetermined threshold.

2. The system of claim 1, further comprising a circuit that is configured to calculate an angle α that is a function of dg/dt and wherein the device monitor is also configured to display an arrow that is angled from horizontal by the angle α.

3. The system of claim 1, wherein the perceptible alarm comprises an alarm selected from a list consisting of: a blinking display, a brightly colored display, a vibratory alarm, an audible alarm, and combinations thereof.

4. The system of claim 1, wherein the display is configured to show different smoothed CGM values as corresponding different colors.

5. The system of claim 1, wherein the display is further configured to display a trend box that indicates a CGM data trend.

6. A method of monitoring glucose in a patient, comprising the steps of: (a) receiving from a continuous glucose monitoring (CGM) device a periodic series of glucose levels in the patient; (b) evaluating a differential change in glucose level over time (dg/dt) based on the series of glucose levels by employing a deconvolution algorithm; (c) generating a smoothed glucose level that is indicative of the series of glucose levels; (d) estimating a dynamic risk based on the smoothed CGM and dg/dt; (e) comparing the dynamic risk to a predetermined threshold; and (f) generating a display representative of the smoothed CGM and generating a perceptible alarm when the dynamic risk is greater than the predetermined threshold.

7. The method of claim 6, further comprising the step of displaying an arrow, such as a colored arrow, indicative of a dg/dt trend.

8. The method of claim 7, further comprising the steps of: (a) calculating an angle α that is a function of dg/dt; and (b) displaying the arrow so that it is angled from horizontal by the angle α.

9. The method of claim 6, wherein the perceptible alarm comprises an alarm selected from a list consisting of: a blinking display, a brightly colored display, a vibratory alarm, an audible alarm, and combinations thereof.

10. The method of claim 6, wherein the display shows different smoothed CGM values as corresponding different colors.

11. The method of claim 6, further comprising the step of displaying a trend box that indicates a CGM data trend.

* * * * *